United States Patent [19]
Böttcher et al.

[11] Patent Number: 4,906,642
[45] Date of Patent: Mar. 6, 1990

[54] PYRIDINE DERIVATIVES

[75] Inventors: Henning Böttcher, Darmstadt; Christoph Seyfried, Seeheim-Jugenheim; Klaus-Otto Minck, Ober-Ramstadt, all of Fed. Rep. of Germany

[73] Assignee: Merck Patent Gesellschaft Mit Beschrankter Haftung, Darmstadt, Fed. Rep. of Germany

[21] Appl. No.: 27,600

[22] Filed: Mar. 18, 1987

[30] Foreign Application Priority Data

Mar. 19, 1986 [DE] Fed. Rep. of Germany ....... 3609142

[51] Int. Cl.$^4$ .................. C07D 401/12; C07D 401/14
[52] U.S. Cl. ...................................... 514/318; 546/20; 546/193; 546/194; 546/255; 546/256
[58] Field of Search ...................... 546/194, 193, 255; 514/318

[56] References Cited

U.S. PATENT DOCUMENTS 3,491,096  1/1970  Baetz et al. .................. 544/238
4,665,187  5/1987  Boettcher et al. .................. 546/255

FOREIGN PATENT DOCUMENTS

DE3438394A1  4/1986  Fed. Rep. of Germany .

Primary Examiner—Joseph P. Brust
Attorney, Agent, or Firm—Millen, White & Zelano

[57] ABSTRACT

New Pyridine derivatives of the formula

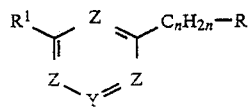

wherein
group Y or one of the groups Z is N and the others of these groups being in each case CH;
n is 1, 2 or 3;
R is

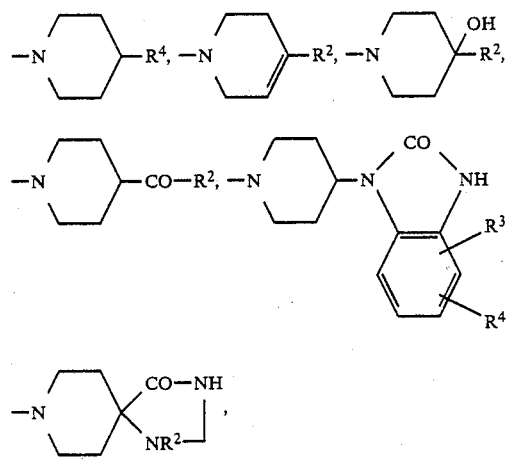

$R^1$ and $R^2$ are in each case phenyl or 2- or 3-thienyl radicals which are unsubstituted or mono- or di-substituted by an alkyl and/or alkoxy having 1-4 C atoms, F, Cl, Br, OH and/or $CF_3$; and
$R^3$ and $R^4$ are in each case H, alkyl or alkoxy having 1-4 C atoms, F, Cl, Br, OH or $CF_3$;
and their salts
with the proviso that, Y is CH when R is

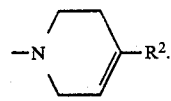

17 Claims, No Drawings

PYRIDINE DERIVATIVES

BACKGROUND OF THE INVENTION

The invention relates to pyridine derivatives and their salts and processes for preparation thereof.

SUMMARY OF THE INVENTION

It is an object of this invention to provide new compounds which can be used for the preparation of medicaments.

Upon further study of the specification and appended claims, further objects and advantages of this invention will become apparent to those skilled in the art.

These objects have been achieved by providing new pyridine derivatives of the formula I

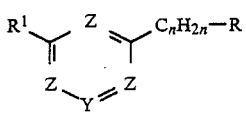                                    I wherein
Y or one of the groups Z is N and the others of these groups being in each case CH,
n is 1, 2 or 3,
R is

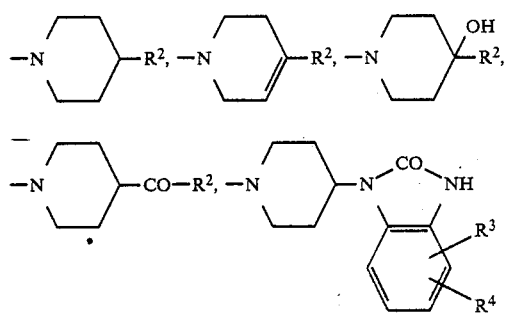

or

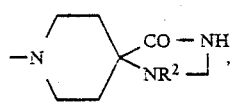

$R^1$ and $R^2$ are in each case phenyl or 2- or 3-thienyl radicals which are unsubstituted or mono- or disubstituted by alkyl and/or alkoxy having 1-4 C atoms, F, Cl, Br, OH and/or $CF_3$ and
$R^3$ and $R^4$ are in each case H, alkyl or alkoxy having 1-4 C atoms, F, Cl, Br, OH or $CF_3$,
but wherein Y is CH if R is

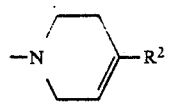

and their salts.

DETAILED DESCRIPTION

It has been found that the substances mentioned have useful pharmacological properties coupled with a good tolerability. Thus, for example, they exhibit effects which influence the central nervous system, preferably suppressing effects (for example sedating, tranquillizing, neuroleptic and/or antidepressant). In detail, the compounds have a suppressing effect on the behavior of mice (for the method, compare Irwin, Psychopharmacologia 13 (1968), 222–257), inhibit apomorphine-induced climbing behavior in mice (for the method compare Costall et al., European J. Pharmacol. 50 (1968), 39–50) or induce contralateral rotatory behavior in hemi-Parkinson rats (detectable by the method of Ungerstedt et al., Brain Res. 24 (1970), 485–493), without noticeable cataleptic side effects occurring (for the method compare Dolini-Stola, Pharmakopsychiat. 6 (1973), 189–197). The substances furthermore inhibit the bonding of tritiated dopamine agonists and antagonists to striatal receptors (detectable by the method of Schwarcz et al., J. Neurochemistry 34 (1980), 772–778, and Creese et al., European J. Pharmacol. 46 (1977), 377–381). The compounds additionally inhibit the tongue-jaw reflex in anaesthetized rats (detectable in accordance with the methods of Barnett et al., European J. Pharmacol. 21 (1973), 178–182, and of Ilhan et al., European J. Pharmacol. 33 (1975), 61–64). Analgesic and antihypertensive effects also arise; thus, the arterial blood pressure measured directly on catheterized conscious spontaneous hypertensive rats (strain SHR/NIH-MO//CHB-EMD; for the method, compare Weeks and Jones, Proc.Soc.Exptl. Biol.Med. 104 (1960), 646–648) is reduced after intragastral administration of the compounds.

Compounds of the formula I and their physiologically acceptable acid addition salts can therefore be used as medicament active compounds and also as intermediate products for the preparation of other medicament active compounds.

A process for the preparation of pyridine derivatives of the formula I and of salts thereof, is characterized in that a compound of the formula II $Py-A-X^1$                                    II wherein
Py is the radical

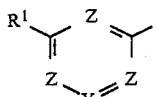

A is the group $-C_nH_{2n}-$,
$X^1$ is X or $NH_2$,
X is Cl, Br, I, OH or a reactively functionally modified OH group and
$R^1$, Y, Z and n have the meanings given,
is reacted with a compound of the formula III $X^2-CH_2CH_2-G-CH_2-X^3$                     III wherein
$X^2$ and $X^3$ are identical or different and, if $X^1$ is $NH_2$, are in each case X, or otherwise together are NH, and
is $-CHR^2-CH_2-$, $-CR^2=CH-$, $-CR^2(OH)-CH_2-$, $-CH(CO-R^2)-CH_2-$,

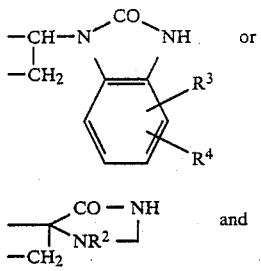

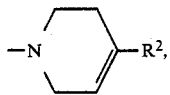

$R^2$, $R^3$ and $R^4$ have the meanings given,
or in that a compound which otherwise corresponds to the formula I but contains one or more reducible groups and/or one or more additional C—C and/or C—N bonds instead of one or more hydrogen atoms is treated with a reducing agent, or in that, to prepare a compound of the formula I wherein R is

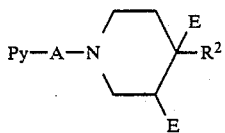

a compound of the formula IV $$Py-A-N\diagup\diagdown{E \atop E}-R^2 \qquad IV$$

wherein
one of the radicals E is X, CN or $NH_2$,
the other radical E is H and
Py, A, $R^2$ and X have the meanings given,
is treated with an agent which splits off HE, and/or in that, if appropriate, an O-alkyl group in a compound of the formula I is split to form an OH group, and/or in that a base of the formula I is converted into one of its salts by treatment with an acid.

The compounds of the formula I include the 2-$R^1$-6-RA-pyridines (I'), the 2-$R^1$-4-RA-pyridines (I''), the 3-$R^1$-5-RA-pyridines (I''') and the 2-RA-4-$R^1$-pyridines (I''''). I''' and I'''' are preferred.

The following compounds may be mentioned specifically:
(4-$R^2$-piperidinoalkyl)-pyridines (Ia), in particular
2-$R^1$-6-(4-$R^2$-piperidinoalkyl)-pyridines (Iaa)
2-$R^1$-4-(4-$R^2$-piperidinoalkyl)-pyridines (Iab)
3-$R^1$-5-(4-$R^2$-piperidinoalkyl)-pyridines (Iac)
2-(4-$R^2$-piperidinoalkyl)-4-$R^1$-pyridines (Iad);
(4-$R^2$-1,2,3,6-tetrahydropyridyl-alkyl)-pyridines (Ib), in particular
2-$R^1$-6-(4-$R^2$-1,2,3,6-tetrahydropyridyl-alkyl)-pyridines (Iba)
2-$R^1$-4-(4-$R^2$-1,2,3,6-tetrahydropyridyl-alkyl)-pyridines (Ibb)
2-(4-$R^2$-1,2,3,6-tetrahydropyridyl-alkyl)-4-$R^1$-pyridines (Ibd);
(4-$R^2$-4-hydroxypiperidinoalkyl)-pyridines (Ic), in particular
2-$R^1$-6-(4-$R^2$-4-hydroxypiperidinoalkyl)-pyridines (Ica)
2-$R^1$-4-(4-$R^2$-4-hydroxypiperidinoalkyl)-pyridines (Icb)
3-$R^1$-5-(4-$R^2$-4-hydroxypiperidinoalkyl)-pyridines (Icc)
2-(4-$R^2$-4-hydroxypiperidinoalkyl)-4-$R^1$-pyridines (Icd);
(4-$R^2$-CO-piperidinoalkyl)-pyridines (Id), in particular
2-$R^1$-6-(4-$R^2$-CO-piperidinoalkyl)-pyridines (Ida)
2-$R^1$-4-(4-$R^2$-CO-piperidinoalkyl)-pyridines (Idb);
3-$R^1$-5-(4-$R^2$-CO-piperidinoalkyl)-pyridines (Idc)
2-(4-$R^2$-CO-piperidinoalkyl)-4-$R^1$-pyridines (Idd);
[4-(2-oxo-4,5,6 or 7-$R^3$4,5,6 or 7-$R^4$-benzimidazolin-1-yl)-piperidinoalkyl]-pyridines (Ie), in particular
2-$R^1$-6-[4-(2-oxo-4,5,6 or 7-$R^3$-4,5,6 or 7-$R^4$-benzimidazolin-1-yl)-piperidinoalkyl]-pyridines (Iea)
2-$R^1$-4-[4-(2-oxo-4,5,6 or 7-$R^3$-4,5,6 or 7-$R^4$-benzimidazolin-1-yl)-piperidinoalkyl]-pyridines (Ieb)
3-$R^1$-5-[4-(2-oxo-4,5,6 or 7-$R^3$-4,5,6 or 7-$R^4$-benzimidazolin-1-yl)-piperidinoalkyl]-pyridines (Iec)
2-[4-(2-oxo-4,5,6 or 7-$R^3$-4,5,6 or 7-$R^4$-benzimidazolin-1-yl)-piperidinoalkyl]-4-$R^1$-pyridines (Ied);
8-pyridylalkyl-1-$R^2$-4-oxo-1,3,8-triazaspiro[4,5]decanes (If), in particular
8-(2-$R^1$-6-pyridylalkyl)-1-$R^2$-4-oxo-1,3,8-triazaspiro[4,5]decanes (Ifa)
8-(2-$R^1$-4-pyridylalkyl)-1-$R^2$-4-oxo-1,3,8-triazaspiro[4,5]decanes (Ifb)
8-(3-$R^1$-5-pyridylalkyl)-1-$R^2$-4-oxo-1,3,8-triazaspiro[4,5]decanes (Ifc)
8-(4-$R^1$-2-pyridylalkyl)-1-$R^2$-4-oxo-1,3,8-triazaspiro[4,5]decanes (Ifd).

Of these groups of compounds, Ia, Ib and Ic are preferred, and specifically, in particular, Iac, Iba, Ibb, Ibd and Icc, and furthermore Iaa, Idc, Iec and Ifc.

In the radicals $R^1$ to $R^4$, alkyl is preferably methyl, and furthermore ethyl, n-propyl, isopropyl, n-butyl, isobutyl, sec.-butyl or tert.-butyl. Alkoxy is preferably methoxy, and furthermore ethoxy, n-propoxy, isopropoxy, n-butoxy, isobutoxy, sec.-butoxy or tert.-butoxy.

The radicals $R^1$ and $R^2$ are preferably unsubstituted phenyl. If $R^1$ and $R^2$ are substituted phenyl groups, these are preferably monosubstituted. However, they can also be disubstituted, in which case the substituents can be identical or different. Preferred substituents on the phenyl groups are methyl, ethyl, methoxy, ethoxy, F, Cl, Br and/or OH. Specifically, $R^1$ and $R^2$ are preferably phenyl, and furthermore o-, m- or p-tolyl, o-, m- or p-ethylphenyl, o-, m- or p-methoxyphenyl, o-, m- or p-ethoxyphenyl, o-, m- or p-fluorophenyl, o-, m- or p-chlorophenyl, o-, m- or p-bromophenyl, o-, m- or p-hydroxyphenyl, o-, m- or p-trifluoromethylphenyl, 2,3-, 2,4-, 2,5-, 2,6-, 3,4- or 3,5-dimethylphenyl, 2,3-, 2,4-, 2,5-, 2,6-, 3,4- or 3,5-dimethoxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dihydroxyphenyl, 2-methyl-4-chlorophenyl, 2- or 3-thienyl or 5-methyl-2-thienyl.

The radicals $R^3$ and $R^4$ can be identical or different. Preferably, they are both H. Furthermore, one of these radicals is preferably H and the other is F, Cl, OH or $CF_3$.

The parameter n is preferably 1 and the group $C_nH_{2n}$ (="A") is preferably —$CH_2$—, and furthermore preferably —$CH(CH_3)$—, —$(CH_2)_2$— or —$(CH_2)_3$—.

The invention accordingly particularly relates to those compounds of the formulae I, I', I'', I''', I'''' and Ia to Ifd in which at least one of the radicals mentioned has one of the abovementioned meanings, in particular one of the abovementioned preferred meanings. Some preferred groups of compounds correspond to the abovementioned formulae, wherein the radicals and parameters which are not described in more detail have the meaning given in the case of formula I, but wherein (a) $R^1$ is phenyl, tolyl, methoxyphenyl, fluorophenyl, chlorophenyl, hydroxyphenyl, trifluoromethylphenyl, dimethoxyphenyl or thienyl (b) $R^1$ is phenyl, o-, m- or p-tolyl, m- or p-methoxyphenyl, p-fluorophenyl, p-chlorophenyl, m- or p-hydroxyphenyl, m-trifluoromethylphenyl, 3,4-dimethoxyphenyl or 2-thienyl;

(c) $R^1$ is phenyl;

(d) $R^2$ is phenyl, tolyl, methoxyphenyl, fluorophenyl, chlorophenyl, trifluoromethylphenyl, chlorotrifluoromethylphenyl or thienyl;

(e) $R^2$ is phenyl, o-, m- or p-tolyl, p-methoxyphenyl, p-fluorophenyl, p-chlorophenyl, m-trifluoromethylphenyl or 2- or 3-thienyl;

(f) $R^2$ is phenyl;

(g) $C_nH_{2n}$ is —CH$_2$—, —CH(CH$_3$)—, —(CH$_2$)$_2$— or —(CH$_2$)$_3$—;

(h) $C_nH_{2n}$ is —CH$_2$—;

(i) $R^1$ is phenyl, o-, m- or p-tolyl, m- or p-methoxyphenyl, p-fluorophenyl, p-chlorophenyl, m- or p-hydroxyphenyl, m-trifluoromethylphenyl, 3,4-dimethoxyphenyl or 2-thienyl, $R^2$ is phenyl, o-, m- or p-tolyl, p-methoxyphenyl, p-fluorophenyl, p-chlorophenyl, m-trifluoromethylphenyl or 2- or 3-thienyl and $C_nH_{2n}$ is —CH$_2$—, —CH(CH$_3$)—, —(CH$_2$)$_2$— or —(CH$_2$)$_3$—;

(j) $R^1$ is phenyl, m- or p-methoxyphenyl, p-fluorophenyl, p-chlorophenyl, m-hydroxyphenyl or 3,4-dimethoxyphenyl, $R^2$ is phenyl and $C_nH_{2n}$ is —CH$_2$—; and (k) $R^1$ and $R^2$ are each phenyl, p-fluorophenyl or p-chlorophenyl and $C_nH_{2n}$ is —CH$_2$—.

Some compounds of the formula I can contain one or more asymmetric carbon atoms. They can therefore be in the form of racemates or, if several asymmetric carbon atoms are present, as mixtures of several racemates as well as in various optically active forms.

The compounds of the formula I are moreover prepared by methods which are known per se, such as are described in the literature (for example in the standard works such as Houben-Weyl, Methoden der Organischen Chemie, (Methods of Organic Chemistry), Georg-Thieme-Verlag, Stuttgart; Organic Reactions, John Wiley & Sons, Inc., New York), and in particular under reaction conditions such as are known and suitable for the reactions mentioned. Use can thereby also be made of variants which are known per se and are not mentioned here in more detail.

If desired, the starting substances for the process claimed can also be formed in situ such that they are not isolated from the reaction mixture but are immediately reacted further to give the compounds of the formula I.

In the compounds of the formula II, $X^1$ is preferably X; accordingly, $X^2$ and $X^3$ in the compounds of the formula III together are preferably NH. The radical X is preferably Cl or Br; however, it can also be I, OH or a reactively functionally modified OH group, in particular alkylsulfonyloxy with 1-6 C atoms (for example methanesulfonyloxy) or arylsulfonyloxy with 6-10 C atoms (for example benzenesulfonyloxy, p-toluenesulfonyloxy or 1- or 2-naphthalenesulfonyloxy).

The compounds of the formula I are accordingly obtainable in particular, by reaction of compounds of the formula Py—A—Cl or Py—A—Br with compounds of the formula III wherein $X^2$ and $X^3$ together denote an NH group (called IIIa below).

The compounds of the formulae II and III are known in some cases; the compounds of the formulae II and III which are not known can easily be prepared analogously to the known compounds. Primary alcohols of the formula Py—A—OH are obtainable, for example, by reduction of the corresponding carboxylic acids or their esters. Treatment with thionyl chloride, hydrogen bromide, phosphorus tribromide or similar halogen compounds gives the corresponding halides of the formula Py—A—Hal. The corresponding sulfonyloxy compounds are obtainable from the alcohols Py—A—OH by reaction with the corresponding sulfonic acid chlorides. The iodine compounds of the formula Py—A—I are obtainable, for example, by the action of potassium iodide on the associated p-toluenesulfonic acid esters. The amines of the formula Py—A—NH$_2$ can be prepared, for example, from the halides with potassium phthalimide or by reduction of the corresponding nitriles.

The compounds of the formula IIIa are known in some cases (for example German Offenlegungsschrift 2,060,816) and are obtainable, for example, by reaction of 4-piperidone with organometallic compounds of the formula M-$R^2$ (wherein M is an Li atom or MgHal), subsequent hydrolysis to give the corresponding 4-$R^2$-4-hydroxypiperidines and, if desired, subsequent dehydration to give 4-$R^2$-3,4-dehydro-piperidines and hydrogenation to give 4-$R^2$-piperidines. Compounds of the formula III ($X^2$ and $X^3=$ in each case X) can be prepared, for example, by reduction of diesters of the formula alkylOOC—CH$_2$—G—COOalkyl to give diols of the formula HO—CH$_2$CH$_2$—G—CH$_2$OH (III, $X^2=X^3=$OH) and, if appropriate, subsequent reaction with SOCl$_2$ or PBr$_3$.

The reaction of the compounds II and III proceeds by methods such as are known from the literature for the alkylation of amines. The components can be fused with one another, if appropriate in a closed tube or in an autoclave, without the presence of a solvent. However, it is also possible to react the compounds in the presence of an inert solvent. Examples of suitable solvents are hydrocarbons, such as benzene, toluene and xylene; ketones, such as acetone and butanone; alcohols, such as methanol, ethanol, isopropanol and n-butanol; ethers, such as tetrahydrofuran (THF) or dioxane; amides, such as dimethylformamide (DMF) or N-methyl-pyrrolidone; and nitriles, such as acetonitrile, and if appropriate also mixtures of these solvents with one another or mixtures with water. The addition of an acid-binding agent, for example an alkali metal hydroxide, carbonate or bicarbonate or alkaline earth metal hydroxide, carbonate or bicarbonate or of another alkali metal or alkaline earth metal salt of a weak acid, preferably a potassium, sodium or calcium salt, or the addition of an organic base, such as triethylamine, dimethylaniline, pyridine or quinoline, or of an excess of the amine component Py—A—NH$_2$ or of the compound of the formula IIIa may be advantageous. The reaction time is from about a few minutes to about 14 days, depending on the conditions used, and the reaction temperature is about 0° to 150° C., usually about 20° to 130° C.

It is furthermore possible to obtain a compound of the formula I by treating a precursor which contains one or more reducible group(s) and/or one or more additional C-C and/or C-N bond(s) instead of hydrogen atoms with a reducing agent, preferably at temperatures of about −80° to +250° C., in the presence of at least one inert solvent.

Reducible groups (groups which are replaceable by hydrogen) are, in particular, oxygen in a carbonyl group, hydroxyl, arylsulfonyloxy (for example p-toluenesulfonyloxy), N-benzenesulfonyl, N-benzyl or O-benzyl.

It is in principle possible for compounds which contain only one of these groups or additional bonds or those which contain two or more of these groups or additional bonds side by side to be converted into a compound of the formula I by reduction. Use is preferably made here of nascent hydrogen or complex metal hydrides, and also of Wolff-Kishner reduction.

Preferred starting substances for the reduction correspond to the formula V $$Py-L-R \qquad V$$

wherein
L is a chain corresponding to the radical A, but wherein one or more —$CH_2$— group(s) are replaced by —CO— group(s) and/or one or more hydrogen atom(s) are replaced by OH group(s).

In the compounds of the formula V, L is preferably —$(CH_2)_{n-1}$—CO—[specifically —CO—, —$CH_2$—CO— or —$CH_2CH_2$—CO—], and furthermore, for example, —$CH(CH_3)$—CO—, —$COCH_2$—, —CO—CO—, —$COCH_2CO$—, —CO—$CH_2CH_2$—, —$CH_2CO$—$CH_2$—, —CHOH—, —$CH_2$—CHOH—, —$(CH_2)_2$—CHOH—, —CHOH—$CH_2$— or —CHOH—CO—.

Compounds of the formula V can be prepared, for example, by reaction of IIIa with a compound of the formula VI $$Py-L-X^1 \qquad VI$$

wherein
Py, L and $X^1$ have the abovementioned meanings, under the conditions described above for the reaction of II and III.

If nascent hydrogen is used as the reducing agent, this can be produced, for example, by treatment of metals with weak acids or with bases. Thus, for example, a mixture of zinc with an alkali metal hydroxide solution or iron with acetic acid can be used. The use of sodium or another alkali metal in an alcohol, such as ethanol, isopropanol, butanol or amyl or isoamyl alcohol or phenol is also suitable. An aluminium/nickel alloy in alkaline-aqueous solution, if appropriate with the addition of ethanol, can furthermore be used. Sodium amalgam or aluminium amalgam in aqueous-alcoholic or aqueous solution are also suitable for producing nascent hydrogen. The reaction can also be carried out in a heterogeneous phase system, an aqueous phase and a benzene or toluene phase advantageously being used.

Complex metal hydrides, such as $LiAlH_4$, $NaBH_4$, diisobutylaluminium hydride or $NaAl(OCH_2CH_2OCH_3)_2H_2$, as well as diborane can furthermore be particularly advantageously used as the reducing agent, if desired with the addition of catalysts, such as $BF_3$, $AlCl_3$ or LiBr. Particularly suitable solvents for this are ethers, such as diethyl ether, di-n-butyl ether, tetrahydrofuran, dioxane, diglyme or 1,2-dimethoxyethane, and hydrocarbons, such as benzene. Suitable solvents for reduction with $NaBH_4$ are primarily alcohols, such as methanol or ethanol, and furthermore water and aqueous alcohols. The reduction by these methods is preferably carried out at temperatures of about −80° to +150° C., in particular about 0° to about 100° C.

—CO— groups in acid amides (for example those of the formula V wherein L is —$(CH_2)_{n-1}$—CO—) can be particularly advantageously reduced to $CH_2$ groups with $LiAlH_4$ in tetrahydrofuran at temperatures of about 0° to 66° C.

It is furthermore possible for one or more carbonyl groups to be reduced to $CH_2$ groups by the Wolff-Kishner method, for example by treatment with anhydrous hydrazine in absolute ethanol under pressure at temperatures between about 150° and 250°. Sodium alcoholate is advantageously used as the catalyst. The reduction can also be varied according to the method of Huang-Minlon, by reaction with hydrazine hydrate in a high-boiling water-miscible solvent, such as diethylene glycol or triethylene glycol, in the presence of an alkali, such as sodium hydroxide. The reaction mixture is as a rule boiled for about 3-4 hours. The water is then distilled off and the hydrazone formed is decomposed at temperatures up to about 200°. The Wolff-Kishner reduction can also be carried out at room temperature in dimethylsulfoxide with hydrazine.

Compounds of the formula I wherein R is a 4-$R^2$-1,2,3,6-tetrahydropyridyl group are furthermore obtained by splitting off HE from compounds of the formula IV to form a double bond. Depending on the definition of E, this reaction can be, for example, splitting off of hydrogen halide, water (dehydration), a carboxylic acid or another acid, ammonia or HCN. The starting substances of the formula IV are obtainable, for example, by reaction of II ($X^1=X$) with a compound of the formula VII

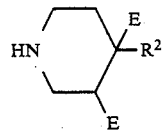

wherein E and $R^2$ have the meanings given.

If one of the radicals E is Hal, this substituent can easily be eliminated under basic reaction conditions. Bases which can be used are: alkali metal hydroxides, alkali metal carbonates, alcoholates, such as, for example, potassium tert.-butylate, and amines, such as, for example, dimethylaniline, pyridine, collidine or quinoline; examples of solvents which are used are benzene, toluene, cyclohexane, tetrahydrofuran or tert.-butanol. The amines used as bases can also be used in excess as the solvent. If one of the radicals E is an OH group, acids, such as acetic acid, hydrochloric acid or mixtures of the two, are preferably used as the dehydrating agent. The addition of a solvent (for example water or ethanol) may be advantageous. Acyl, alkylsulfonyl and alkoxysulfonyloxy or amino radicals can be eliminated under similar conditions. Elimination of sulfonic acid radicals, for example of mesylates or tosylates, is carried out under gentle conditions by boiling in dimethylformamide or dimethylsulfoxide with alkali metal carbonates, for example $Li_2CO_3$, or with potassium acetate. Ammonia can already be split off by heating the salts of the corresponding amino compounds (in particular the 4-amino derivatives). HCN can be split off in a similar manner from compounds of the formula IV (one group E=CN) by heating. Elimination of HE from IV is generally carried out of temperatures between 0° and about 250°, preferably between 50° and 200°.

If appropriate, a compound of the formula I can furthermore be converted into another compound of the formula I by methods which are known per se.

Thus, ethers (O-alkyl derivatives) can be split, the corresponding hydroxy derivatives being formed. For example, the ethers can be split by treatment with a dimethylsulfide-boron tribromide complex, for example in toluene, 1,2-dichloroethane, tetrahydrofuran or dimethylsulfoxide, by fusing with pyridine hydrohalides or aniline hydrohalides, preferably pyridine hydrochloride, at about 150°–250°, with HBr/acetic acid or with Al trihalides in chlorinated hydrocarbons, such as 1,2-dichloroethane.

A resulting base of the formula I can be converted into the associated acid addition salt with an acid. Acids which are preferably suitable for this reaction are those which give physiologically acceptable salts. Thus, inorganic acids can be used, for example sulfuric acid, hydrogen halide acids, such as hydrochloric acid or hydrobromic acid, phosphoric acids, such as orthophosphoric acids, nitric acid and sulfamic acid, and furthermore organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono-and -disulfonic acids and laurylsulfuric acid. Acid addition salts which are not physiologically acceptable (for example picrates) may be suitable for isolation and purification of bases of the formula I.

If desired, the free bases of the formula I can be liberated from their salts by treatment with strong bases, such as sodium hydroxide or potassium hydroxide or sodium carbonate or potassium carbonate.

The invention furthermore relates to the use of the compounds of the formula I and their physiologically acceptable salts for the preparation of pharmaceutical formulations, in particular by a non-chemical route. They can thereby be brought into a suitable dosage form together with at least one excipient or auxiliary and if appropriate in combination with one or more other active compound(s).

The invention furthermore relates to agents, in particular pharmaceutical formulations, containing at least one compound of the formula I and/or one of its physiologically acceptable salts. These formulations can be used as medicaments in human or veterinary medicine. Possible excipients are organic or inorganic substances which are suitable for enteral (for example oral) or parenteral administration or topical application and with which the new compounds do not react, for example water, vegetable oils, benzyl alcohols, polyethylene glycols, gelatine, carbohydrates, such as lactose or starch, magnesium stearate, talc or vaseline. Tablets, coated tablets, capsules, syrups, elixirs, drops or suppositories are used, in particular, for enteral administration, solutions, preferably oily or aqueous solutions, and furthermore suspensions, emulsions or implants are used for parenteral administration and ointments, creams or powders are used topically. The new compounds can also be lyophilized and the resulting lyophilizates can be used, for example, to prepare injection preparations.

The formulations mentioned can be sterilized and/or can contain auxiliaries, such as lubricants, preservatives, stabilizers and/or wetting agents, emulsifiers, salts for influencing the osmotic pressure, buffer substances, dyestuffs, flavor substances and/or aroma substances. If desired, they can also contain one or more other active compounds, for example one or more vitamins.

The invention furthermore relates to the use of the compounds of the formula I and their physiologically acceptable salts in the therapeutic treatment of the human or animal body and in combating illnesses, in particular schizophrenia, psychoreactive disturbance and psychopathy, depression, severe chronic pain and illnesses associated with increased blood pressure. The compounds thus are valuable neuroleptics, particularly antipsychotics.

The compounds can furthermore be used in the treatment of extrapyramidal disturbances.

The substances according to the invention are thereby as a rule administered analogously to known commercially available preparations (thioridazine and haloperidol), preferably in dosages of about 0.2 to 500 mg, in particular about 0.2 to 50 mg per dosage unit. The daily dosage is preferably about 0.003 to 10 mg/kg of body weight.

The specific dose for each particular patient depends, however, on the most diverse factors, for example on the efficacy of the specific compound employed, and on the age, body weight, general state of health, sex, diet, time and route of administration, rate of excretion and medicament combination and the severity of the particular illness to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight. Also, in the following examples, "customary working up" means: water is added, if necessary, the mixture is extracted with methylene chloride, the organic phase is separated off, dried over sodium sulfate, filtered and evaporated and the residue is purified by chromatography on silica gel and/or by crystallization.

EXAMPLES

EXAMPLE 1

A solution of 24 g of 2-chloromethyl-4-phenylpyridine hydrochloride (obtainable by reduction of 4-phenylpyridine-2-carboxylic acid with LiAlH$_4$ to give 2-hydroxymethyl-b 4-phenyl-pyridine and reaction with SOCl$_2$), 16 g of 4-phenyl-1,2,3,6-tetrahydropyridine and 22 ml of triethylamine in 300 ml of acetonitrile is boiled for 12 hours and worked up in the customary manner to give 2-(4-phenyl-1,2,3,6-tetrahydropyridylmethyl)-4-phenyl-pyridine ("P"), dihydrochloride, m.p. 223° (decomposition).

The following compounds are obtained analogously from the corresponding methanesulfonates, chlorides or bromines:

2-(4-phenyl-1,2,3,6-tetrahydropyridyl-methyl)-4-o-tolylpyridine
2-(4-phenyl-1,2,3,6-tetrahydropyridyl-methyl)-4-m-tolylpyridine
2-(4-phenyl-1,2,3,6-tetrahydropyridyl-methyl)-4-p-tolylpyridine
2-(4-phenyl-1,2,3,6-tetrahydropyridyl-methyl)-4-m-methoxyphenyl-pyridine
2-(4-phenyl-1,2,3,6-tetrahydropyridyl-methyl)-4-p-methoxyphenyl-pyridine
2-(4-phenyl-1,2,3,6-tetrahydropyridyl-methyl)-4-p-fluorophenyl-pyridine
2-(4-phenyl-1,2,3,6-tetrahydropyridyl-methyl)-4-p-chlorophenyl-pyridine
2-(4-phenyl-1,2,3,6-tetrahydropyridyl-methyl)-4-m-hydroxyphenyl-pyridine
2-(4-phenyl-1,2,3,6-tetrahydropyridyl-methyl)-4-p-hydroxyphenyl-pyridine
2-(4-phenyl-1,2,3,6-tetrahydropyridyl-methyl)-4-m-trifluoromethylphenyl-pyridine
2-(4-phenyl-1,2,3,6-tetrahydropyridyl-methyl)-4-(3,4-dimethoxyphenyl)-pyridine
2-(4-phenyl-1,2,3,6-tetrahydropyridyl-methyl)-4-(2-thienyl)-pyridine
2-(4-o-tolyl-1,2,3,6-tetrahydropyridyl-methyl)-4-phenylpyridine
2-(4-m-tolyl-1,2,3,6-tetrahydropyridyl-methyl)-4-phenylpyridine
2-(4-p-tolyl-1,2,3,6-tetrahydropyridyl-methyl)-4-phenylpyridine
2-(4-p-methoxyphenyl-1,2,3,6-tetrahydropyridyl-methyl)-4-phenyl-pyridine
2-(4-p-fluorophenyl-1,2,3,6-tetrahydropyridyl-methyl)-4-phenyl-pyridine
2-(4-p-chlorophenyl-1,2,3,6-tetrahydropyridyl-methyl)-4-phenyl-pyridine
2-(4m-trifluoromethylphenyl-1,2,3,6-tetrahydropyridyl-methyl)-4-phenyl-pyridine
2-[4-(4-chloro-3-trifluoromethylphenyl)-1,2,3,6-tetrahydropyridyl-methyl]-4-phenyl-pyridine
2-[4-(2-thienyl)-1,2,3,6-tetrahydropyridyl-methyl]-4-phenyl-pyridine
2-[4-(2-thienyl)-1,2,3,6-tetrahydropyridyl-methyl]-4-m-tolyl-pyridine
2-[4-(2-thienyl)-1,2,3,6-tetrahydropyridyl-methyl]-4-p-tolyl-pyridine
2-[4-(2-thienyl)-1,2,3,6-tetrahydropyridyl-methyl]-4-p-fluorophenyl-pyridine
2-[4-(3-thienyl)-1,2,3,6-tetrahydropyridyl-methyl]-4-phenyl-pyridine
2-[1-(4-phenyl-1,2,3,6-tetrahydropyridyl)-ethyl]-4-phenyl-pyridine
2-[1-(4-phenyl-1,2,3,6-tetrahydropyridyl)-ethyl]-4-m-methoxyphenyl-pyridine
2-[1-(4-phenyl-1,2,3,6-tetrahydropyridyl)-ethyl]-4-p-methoxyphenyl-pyridine
2-[2-(4-phenyl-1,2,3,6-tetrahydropyridyl)-ethyl]-4-phenyl-pyridine
2-[2-(4-phenyl-1,2,3,6-tetrahydropyridyl)-ethyl]-4-m-methoxyphenyl-pyridine
2-[2-(4-phenyl-1,2,3,6-tetrahydropyridyl)-ethyl]-4-p-methoxyphenyl-pyridine
2-[3-(4-phenyl-1,2,3,6-tetrahydropyridyl)-propyl]-4-phenyl-pyridine
2-[3-(4-phenyl-1,2,3,6-tetrahydropyridyl)-propyl]-4-m-methoxyphenyl-pyridine
2-[3-(4-phenyl-1,2,3,6-tetrahydropyridyl)-propyl]-4-p-methoxyphenyl-pyridine
2-(4-p-fluorophenyl-1,2,3,6-tetrahydropyridyl-methyl)-4-p-fluorophenyl-pyridine
2-[1-(4-p-fluorophenyl-1,2,3,6-tetrahydropyridyl)-ethyl]-4-p-fluorophenyl-pyridine
2-[2-(4-p-fluorophenyl-1,2,3,6-tetrahydropyridyl)-ethyl]-4-p-fluorophenyl-pyridine
2-[3-(4-p-fluorophenyl-1,2,3,6-tetrahydropyridyl)-propyl]-4-p-fluorophenyl-pyridine
2-[2-(4-(2-thienyl)-1,2,3,6-tetrahydropyridyl)-ethyl]-4-phenyl-pyridine
2-[3-(4-(2-thienyl)-1,2,3,6-tetrahydropyridyl)-propyl]-4-phenyl-pyridine
2-phenyl-6-(4-phenylpiperidinomethyl)-pyridine
2-phenyl-6-(4-p-fluorophenylpiperidinomethyl)-pyridine
2-phenyl-6-(4-p-chlorophenylpiperidinomethyl)-pyridine
2-p-fluorophenyl-6-(4-phenylpiperidinomethyl)-pyridine
2-p-fluorophenyl-6-(4-p-fluorophenylpiperidinomethyl)-pyridine
2-p-fluorophenyl-6-(4-p-chlorophenylpiperidinomethyl)-pyridine
2-p-chlorophenyl-6-(4-phenylpiperidinomethyl)-pyridine
2-p-chlorophenyl-6-(4-p-fluorophenylpiperidinomethyl)-pyridine
2-p-chlorophenyl-6-(4-p-chlorophenylpiperidinomethyl)-pyridine
2-phenyl-4-(4-phenylpiperidinomethyl)-pyridine, dihydrochloride, m.p. 241°–243°
2-phenyl-4-(4-p-fluorophenylpiperidinomethyl)-pyridine
2-phenyl-4-(4-p-chlorophenylpiperidinomethyl)-pyridine
2-p-fluorophenyl-4-(4-phenylpiperidinomethyl)-pyridine
2-p-fluorophenyl-4-(4-p-fluorophenylpiperidinomethyl)-pyridine
2-p-fluorophenyl-4-(4-p-chlorophenylpiperidinomethyl)-pyridine
2-p-chlorophenyl-4-(4-phenylpiperidinomethyl)-pyridine
2-p-chlorophenyl-4-(4-p-fluorophenylpiperidinomethyl)-pyridine
2-p-chlorophenyl-4-(4-p-chlorophenylpiperidinomethyl)-pyridine
3-phenyl-5-(4-phenylpiperidinomethyl)-pyridine dihydrochloride trihydrate, m.p. 99°–101°; malonate, m.p. 167° (dec.); maleate, m.p. 194°; difumarate, m.p. 181°; succinate, m.p. 121°
3-phenyl-5-(4-p-fluorophenylpiperidinomethyl)-pyridine, dihydrochloride, m.p. 230°–233°
3-phenyl-5-(4-p-chlorophenylpiperidinomethyl)-pyridine
3-p-fluorophenyl-5-(4-phenylpiperidinomethyl)-pyridine, malonate, m.p. 142°–143°
3-p-fluorophenyl-5-(4-p-fluorophenylpiperidinomethyl)-pyridine
3-p-fluorphenyl-5-(4-p-chlorophenylpiperidinomethyl)-pyridine
3-p-chlorophenyl-5-(4-phenylpiperidinomethyl)-pyridine 3-p-chlorophenyl-5-(4-p-fluorophenylpiperidinomethyl)-pyridine
3-p-chlorophenyl-5-(4-p-chlorophenylpiperidinomethyl)-pyridine
2-(4-phenylpiperidinomethyl)-4-phenyl-pyridine, dihydrochloride - dihydrate, m.p. 214°
2-(4-p-fluorophenylpiperidinomethyl)-4-phenyl-pyridine
2-(4-p-chlorophenylpiperidinomethyl)-4-phenyl-pyridine
2-(4-phenylpiperidinomethyl)-4-p-fluorophenyl-pyridine
2-(4-p-fluorophenylpiperidinomethyl)-4-p-fluorophenyl-pyridine
2-(4-p-chlorophenylpiperidinomethyl)-4-p-fluorophenyl-pyridine
2-(4-phenylpiperidinomethyl)-4-p-chlorophenyl-pyridine
2-(4-p-fluorophenylpiperidinomethyl)-4-p-chlorophenyl-pyridine
2-(4-p-chlorophenylpiperidinomethyl)-4-p-chlorophenyl-pyridine
3-phenyl-5-[2-(4-phenylpiperidino)-ethyl]-pyridine, m.p. 89°–91°
3-phenyl-5-[2-(4-p-fluorophenylpiperidino)-ethyl]-pyridine
3-phenyl-5-[2-(4-p-chlorophenylpiperidino)-ethyl]-pyridine
3-p-fluorophenyl-5-[2-(4-phenylpiperidino)-ethyl]-pyridine
3-p-fluorophenyl-5-[2-(4-p-fluorophenylpiperidino)-ethyl]-pyridine
3-p-fluorophenyl-5-[2-(4-p-chlorophenylpiperidino)-ethyl]-pyridine
3-p-chlorophenyl-5-[2-(4-phenylpiperidino)-ethyl]-pyridine
3-chlorophenyl-5-[2-(4-p-fluorophenylpiperidino)-ethyl]-pyridine
3-chlorophenyl-5-[2-(4-p-chlorophenylpiperidino)-ethyl]-pyridine
2-phenyl-6-(4-phenyl-1,2,3,6-tetrahydropyridyl-methyl)-pyridine hydrochloride, m.p. 206°–208°
2-phenyl-6-(4-p-fluorophenyl-1,2,3,6-tetrahydropyridylmethyl)-pyridine
2-phenyl-6-(4-p-chlorophenyl-1,2,3,6-tetrahydropyridylmethyl)-pyridine
2-p-fluorophenyl-6-(4-phenyl-1,2,3,6-tetrahydropyridylmethyl)-pyridine
2-p-fluorophenyl-6-(4-p-fluorophenyl-1,2,3,6-tetrahydropyridyl-methyl)-pyridine
2-p-fluorophenyl-6-(4-p-chlorophenyl-1,2,3,6-tetrahydropyridyl-methyl)-pyridine
2-p-chlorophenyl-6-(4-phenyl-1,2,3,6-tetrahydropyridyl-methyl)-pyridine
2-p-chlorophenyl-6-(4-p-fluorophenyl-1,2,3,6-tetrahydropyridyl-methyl)-pyridine
2-p-chlorophenyl-6-(4-p-chlorophenyl-1,2,3,6-tetrahydropyridyl-methyl)-pyridine
2-phenyl-4-(4-phenyl-1,2,3,6-tetrahydropyridyl-methyl)-pyridine
2-phenyl-4-(4-p-fluorophenyl-1,2,3,6-tetrahydropyridyl-methyl)-pyridine
2-phenyl-4-(4-p-chlorophenyl-1,2,3,6-tetrahydropyridyl-methyl)-pyridine
2-p-fluorophenyl-4-(4-phenyl-1,2,3,6-tetrahydropyridyl-methyl)-pyridine
2-p-fluorophenyl-4-(4-p-fluorophenyl-1,2,3,6-tetrahydropyridyl-methyl)-pyridine
2-p-fluorophenyl-4-(4-p-chlorophenyl-1,2,3,6-tetrahydropyridyl-methyl)-pyridine
2-p-chlorophenyl-4-(4-phenyl-1,2,3,6-tetrahydropyridylmethyl)-pyridine
2-p-chlorophenyl-4-(4-p-fluorophenyl-1,2,3,6-tetrahydropyridyl-methyl)-pyridine
2-p-chlorophenyl-4-(4-p-chlorophenyl-1,2,3,6-tetrahydropyridyl-methyl)-pyridine
2-phenyl-6-(4-phenyl-4-hydroxypiperidinomethyl)-pyridine
2-phenyl-6-(4-p-fluorophenyl-4-hydroxypiperidinomethyl)-pyridine
2-phenyl-6-(4-p-chlorophenyl-4-hydroxypiperidinomethyl)-pyridine
2-p-fluorophenyl-6-(4-phenyl-4-hydroxypiperidinomethyl)-pyridine
2-p-fluorophenyl-6-(4-p-fluorophenyl-4-hydroxypiperidinomethyl)-pyridine
2-p-fluorophenyl-6-(4-p-chlorophenyl-4-hydroxypiperidinomethyl)-pyridine
2-p-chlorophenyl-6-(4-phenyl-4-hydroxypiperidinomethyl)-pyridine
2-p-chlorophenyl-6-(4-p-fluorophenyl-4-hydroxypiperidinomethyl)-pyridine
2-p-chlorophenyl-6-(4-p-chlorophenyl-4-hydroxypiperidinomethyl)-pyridine
2-phenyl-4-(4-phenyl-4-hydroxypiperidinomethyl)-pyridine
2-phenyl-4-(4-p-fluorophenyl-4-hydroxypiperidinomethyl)-pyridine
2-phenyl-4-(4-p-chlorophenyl-4-hydroxypiperidinomethyl)-pyridine, m.p. 149°–151°
2-p-fluorophenyl-4-(4-phenyl-4-hydroxypiperidinomethyl)-pyridine
2-p-fluorophenyl-4-(4-p-fluorophenyl-4-hydroxypiperidinomethyl)-pyridine
2-p-fluorophenyl-4-(4-p-chlorophenyl-4-hydroxypiperidinomethyl)-pyridine
2-p-chlorophenyl-4-(4-phenyl-4-hydroxypiperidinomethyl)-pyridine
2-p-chlorophenyl-4-(4-p-fluorophenyl-4-hydroxypiperidinomethyl)-pyridine
2-p-chlorophenyl-4-(4-p-chlorophenyl-4-hydroxypiperidinomethyl)-pyridine
3-phenyl-5-(4-phenyl-4-hydroxypiperidinomethyl)-pyridine
3-phenyl-5-(4-p-fluorophenyl-4-hydroxypiperidinomethyl)-pyridine
3-phenyl-5-(4-p-chlorophenyl-4-hydroxypiperidinomethyl)-pyridine, hydrochloride, m.p. 246°–247°
3-p-fluorophenyl-5-(4-phenyl-4-hydroxypiperidinomethyl)-pyridine, m.p. 157°–159°
3-p-fluorophenyl-5-(4-p-fluorophenyl-4-hydroxypiperidinomethyl)-pyridine
3-p-fluorophenyl-5-(4-p-chlorophenyl-4-hydroxypiperidinomethyl)-pyridine hydrochloride, m.p. 233°–234°
3-p-chlorophenyl-5-(4-phenyl-4-hydroxypiperidinomethyl)-pyridine
3-p-chlorophenyl-5-(4-p-fluorophenyl-4-hydroxypiperidinomethyl)-pyridine
3-p-chlorophenyl-5-(4-p-chlorophenyl-4-hydroxypiperidinomethyl)-pyridine
2-(4-phenyl-4-hydroxypiperidinomethyl)-4-phenyl-pyridine
2-(4-p-fluorophenyl-4-hydroxypiperidinomethyl)-4-phenyl-pyridine 2-(4-p-chlorophenyl-4-hydroxypiperidinomethyl)-4-phenyl-pyridine
2-(4-phenyl-4-hydroxypiperidinomethyl)-4-p-fluorophenyl-pyridine
2-(4-p-fluorophenyl-4-hydroxypiperidinomethyl)-4-p-fluorophenyl-pyridine
2-(4-p-chlorophenyl-4-hydroxypiperidinomethyl)-4-p-fluorophenyl-pyridine
2-(4-phenyl-4-hydroxypiperidinomethyl)-4-p-chlorophenyl-pyridine
2-(4-p-fluorophenyl-4-hydroxypiperidinomethyl)-4-p-chlorophenyl-pyridine
2-(4-p-chlorophenyl-4-hydroxypiperidinomethyl)-4-p-chlorophenyl-pyridine
2-phenyl-6-(4-benzoylpiperidinomethyl)-pyridine
2-phenyl-6-(4-p-fluorobenzoylpiperidinomethyl)-pyridine
2-phenyl-6-(4-p-chlorobenzoylpiperidinomethyl)-pyridine
2-p-fluorophenyl-6-(4-benzoylpiperidinomethyl)-pyridine
2-p-fluorophenyl-6-(4-p-fluorobenzoylpiperidinomethyl)-pyridine
2-p-fluorophenyl-6-(4-p-chlorobenzoylpiperidinomethyl)-pyridine
2-p-chlorophenyl-6-(4-benzoylpiperidinomethyl)-pyridine
2-p-chorophenyl-6-(4-p-fluorobenzoylpiperidinomethyl)-pyridine
2-p-chlorophenyl-6-(4-p-chlorobenzoylpiperidinomethyl)-pyridine
2-phenyl-4-(4-benzoylpiperidinomethyl)-pyridine
2-phenyl-4-(4-p-fluorobenzoylpiperidinomethyl)-pyridine
2-phenyl-4-(4-p-chlorobenzoylpiperidinomethyl)-pyridine
2-p-fluorophenyl-4-(4-benzoylpiperidinomethyl)-pyridine
2-p-fluorophenyl-4-(4-p-fluorobenzoylpiperidinomethyl)-pyridine
2-p-fluorophenyl-4-(4-p-chlorobenzoylpiperidinomethyl)-pyridine
2-p-chlorophenyl-4-(4-benzoylpiperidinomethyl)-pyridine
2-p-chlorophenyl-4-(4-p-fluorobenzoylpiperidinomethyl)-pyridine
2-p-chlorophenyl-4-(4-p-chlorobenzoylpiperidinomethyl)-pyridine
3-phenyl-5-(4-benzoylpiperidinomethyl)-pyridine
3-phenyl-5-(4-p-fluorobenzoylpiperidinomethyl)-pyridine, m.p. 91°–93°
3-phenyl-5-(4-p-chlorobenzoylpiperidinomethyl)-pyridine
3-p-fluorophenyl-5-(4-benzoylpiperidinomethyl)-pyridine
3-p-fluorophenyl-5-(4-p-fluorobenzoylpiperidinomethyl)-pyridine
3-p-fluorophenyl-5-(4-p-chlorobenzoylpiperidinomethyl)-pyridine
3-p-chlorophenyl-5-(4-benzoylpiperidinomethyl)-pyridine
3-p-chlorophenyl-5-(4-p-fluorobenzoylpiperidinomethyl)-pyridine
3-p-chlorophenyl-5-(4-p-chlorobenzoylpiperidinomethyl)-pyridine
2-(4-benzoylpiperidinomethyl)-4-phenyl-pyridine
2-(4-p-fluorobenzoylpiperidinomethyl)-4-phenyl-pyridine
2-(4-p-chlorobenzoylpiperidinomethyl)-4-phenyl-pyridine
2-(4-benzoylpiperidinomethyl)-4-p-fluorophenyl-pyridine
2-(4-p-fluorobenzoylpiperidinomethyl)-4-p-fluorophenyl-pyridine
2-(4-chlorobenzoylpiperidinomethyl)-4-p-fluorophenyl-pyridine
2-(4-benzoylpiperidinomethyl)-4-p-chlorophenyl-pyridine
2-(4-p-fluorobenzoylpiperidinomethyl)-4-p-chlorophenyl-pyridine
2-(4-p-chlorobenzoylpiperidinomethyl)-4-p-chlorophenyl-pyridine
2-phenyl-6-[4-(2-oxobenzimidazolin-1-yl)-piperidinomethyl]-pyridine
2-phenyl-6-[4-(2-oxo-5-fluorobenzimidazolin-1-yl)-piperidinomethyl]-pyridine
2-phenyl-6-[4-(2-oxo-5-chlorobenzimidazolin-1-yl)-piperidinomethyl]-pyridine
2-p-fluorophenyl-6-[4-(2-oxobenzimidazolin-1-yl)-piperidinomethyl]-pyridine
2-p-fluorophenyl-6-[4-(2-oxo-5-fluorobenzimidazolin-1-yl)-piperidinomethyl]-pyridine
2-p-fluorophenyl-6-[4-(2-oxo-5-chlorobenzimidazolin-1-yl)-piperidinomethyl]-pyridine
2-p-chlorophenyl-6-[4-(2-oxobenzimidazolin-1-yl)-piperidinomethyl]-pyridine
2-p-chlorophenyl-6-[4-(2-oxo-5-fluorobenzimidazolin-1-yl)-piperidinomethyl]-pyridine
2-p-chlorophenyl-6-[4-(2-oxo-5-chlorobenzimidazolin-1-yl)-piperidinomethyl]-pyridine
2-phenyl-4-[4-(2-oxobenzimidazolin-1-yl)-piperidinomethyl]-piperidine, m.p. 203°–205°
2-phenyl-4-[4-(2-oxo-5-fluorobenzimidazolin-1-yl)-piperidinomethyl]-pyridine
2-phenyl-4-[4-(2-oxo-5-chlorobenzimidazolin-1-yl)-piperidinomethyl]-pyridine
2-p-fluorophenyl-4-[4-(2-oxobenzimidazolin-1-yl)-piperidinomethyl]-pyridine
2-p-fluorophenyl-4-[4-(2-oxo-5-fluorobenzimidazolin-1-yl)-piperidinomethyl]-pyridine
2-p-fluorophenyl-4-[4-(2-oxo-5-chlorobenzimidazolin-1-yl)-piperidinomethyl]-pyridine
2-p-chlorophenyl-4-[4-(2-oxobenzimidazolin-1-yl)-piperidinomethyl]-pyridine
2-p-chlorophenyl-4-[4-(2-oxo-5-fluorobenzimidazolin-1-yl)-piperidinomethyl]-pyridine
2-p-chlorophenyl-4-[4-(2-oxo-5-chlorobenzimidazolin-1-yl)-piperidinomethyl]-pyridine
3-phenyl-5-[4-(2-oxobenzimidazolin-1-yl)-piperidinomethyl]-pyridine, m.p. 186°–188°
3-phenyl-5-[4-(2-oxo-5-fluorobenzimidazolin-1-yl)-piperidinomethyl]-pyridine
3-phenyl-5-[4-(2-oxo-5-chlorobenzimidazolin-1-yl)-piperidinomethyl]-pyridine
3-p-fluorophenyl-5-[4-(2-oxobenzimidazolin-1-yl)-piperidinomethyl]-pyridine, dihydrochloride, m.p. 229°–231°
3-p-fluorophenyl-5-[4-(2-oxo-5-fluorobenzimidazolin-1-yl)-piperidinomethyl]-pyridine
3-p-fluorophenyl-5-[4-(2-oxo-5-chlorobenzimidazolin-1-yl)-piperidinomethyl]-pyridine
3-p-chlorophenyl-5-[4-(2-oxobenzimidazolin-1-yl)-piperidinomethyl]-pyridine
3-p-chlorophenyl-5-[4-(2-oxo-5-fluorobenzimidazolin-1-yl)-piperidinomethyl]-pyridine 3-p-chlorophenyl-5-[4-(2-oxo-5-chlorobenzimidazolin-1-yl)-piperidinomethyl]-pyridine
2-[4-(2-oxobenzimidazolin-1-yl)-piperidinomethyl]-4-phenyl-pyridine
2-[4-(2-oxo-5-fluorobenzimidazolin-1-yl)-piperidinomethyl]-4-phenyl-pyridine
2-[4-(2-oxo-5-chlorobenzimidazolin-1-yl)-piperidinomethyl]-4-phenyl-pyridine
2-[4-(2-oxobenzimidazolin-1-yl)-piperidinomethyl]-4-p-fluorophenyl-pyridine
2-[4-(2-oxo-5-fluorobenzimidazolin-1-yl)-piperidinomethyl]-4-p-fluorophenyl-pyridine
2-[4-(2-oxo-5-chlorobenzimidazolin-1-yl)-piperidinomethyl]-4-p-fluorophenyl-pyridine
2-[4-(2-oxobenzimidazolin-1-yl)-piperidinomethyl]-4-p-chlorophenyl-pyridine
2-[4-(2-oxo-5-fluorobenzimidazolin-1-yl)-piperidinomethyl]-4-p-chlorophenyl-pyridine
2-[4-(2-oxo-5-chlorobenzimidazolin-1-yl)-piperidinomethyl]-4-p-chlorophenyl-pyridine
8-(2-phenyl-6-pyridylmethyl)-1-phenyl-4-oxo-1,3,8-triazaspiro[4,5]decane
8-(2-phenyl-6-pyridylmethyl)-1-p-fluorophenyl-4-oxo-1,3,8-triazaspiro[4,5]decane
8-(2-phenyl-6-pyridylmethyl)-1-p-chlorophenyl-4-oxo-1,3,8-triazaspiro[4,5]decane
8-(2-p-fluorophenyl-6-pyridylmethyl)-1-phenyl-4-oxo-1,3,8-triazaspiro[4,5]decane
8-(2-p-fluorophenyl-6-pyridylmethyl)-1-p-fluorophenyl-4-oxo-1,3,8-triazaspiro[4,5]decane
8-(2-p-fluorophenyl-6-pyridylmethyl)-1-p-chlorophenyl-4-oxo-1,3,8-triazaspiro[4,5]decane
8-(2-p-chlorophenyl-6-pyridylmethyl)-1-phenyl-4-oxo-1,3,8-triazaspiro[4,5]decane
8-(2-p-chlorophenyl-6-pyridylmethyl)-1-p-fluorophenyl-4-oxo-1,3,8-triazaspiro[4,5]decane
8-(2-p-chlorophenyl-6-pyridylmethyl)-1-p-chlorophenyl-4-oxo-1,3,8-triazaspiro[4,5]decane
8-(2-phenyl-4-pyridylmethyl)-1-phenyl-4-oxo-1,3,8-triazaspiro[4,5]decane
8-(2-phenyl-4-pyridylmethyl)-1-p-fluorophenyl-4-oxo-1,3,8-triazaspiro[4,5]decane
8-(2-phenyl-4-pyridylmethyl)-1-p-chlorophenyl-4-oxo-1,3,8-triazaspiro[4,5]decane
8-(2-p-fluorophenyl-4-pyridylmethyl)-1-phenyl-4-oxo-1,3,8-triazaspiro[4,5]decane
8-(2-p-fluorophenyl-4-pyridylmethyl)-1-p-fluorophenyl-4-oxo-1,3,8-triazaspiro[4,5]decane
8-(2-p-fluorophenyl-4-pyridylmethyl)-1-p-chlorophenyl-4-oxo-1,3,8-triazaspiro[4,5]decane
8-(2-p-chlorophenyl-4-pyridylmethyl)-1-phenyl-4-oxo-1,3,8-triazaspiro[4,5]decane
8-(2-p-chlorophenyl-4-pyridylmethyl)-1-p-fluorophenyl-4-oxo-1,3,8-triazaspiro[4,5]decane
8-(2-p-chlorophenyl-4-pyridylmethyl)-1-p-chlorophenyl-4-oxo-1,3,8-triazaspiro[4,5]decane
8-(3-phenyl-5-pyridylmethyl)-1-phenyl-4-oxo-1,3,8-triazaspiro[4,5]decane, m.p. 223°-225°
8-(3-phenyl-5-pyridylmethyl)-1-p-fluorophenyl-4-oxo-1,3,8-triazaspiro[4,5]decane
8-(3-phenyl-5-pyridylmethyl)-1-p-chlorophenyl-4-oxo-1,3,8-triazaspiro[4,5]decane
8-(3-p-fluorophenyl-5-pyridylmethyl)-1-phenyl-4-oxo-1,3,8-triazaspiro[4,5]decane
8-(3-p-fluorophenyl-5-pyridylmethyl)-1-p-fluorophenyl-4-oxo-1,3,8-triazaspiro[4,5]decane
8-(3-p-fluorophenyl-5-pyridylmethyl)-1-p-chlorophenyl-4-oxo-1,3,8-triazaspiro[4,5]decane
8-(3-p-chlorophenyl-5-pyridylmethyl)-1-phenyl-4-oxo-1,3,8-triazaspiro[4,5]decane
8-(3-p-chlorophenyl-5-pyridylmethyl)-1-p-fluorophenyl-4-oxo-1,3,8-triazaspiro[4,5]decane
8-(3-p-chlorophenyl-5-pyridylmethyl)-1-p-chlorophenyl-4-oxo-1,3,8-triazaspiro[4,5]decane
8-(4-phenyl-2-pyridylmethyl)-1-phenyl-4-oxo-1,3,8-triazaspiro[4,5]decane
8-(4-phenyl-2-pyridylmethyl)-1-p-fluorophenyl-4-oxo-1,3,8-triazaspiro[4,5]decane
8-(4-phenyl-2-pyridylmethyl)-1-p-chlorophenyl-4-oxo-1,3,8-triazaspiro[4,5]decane
8-(4-p-fluorophenyl-2-pyridylmethyl)-1-phenyl-4-oxo-1,3,8-triazaspiro[4,5]decane
8-(4-p-fluorophenyl-2-pyridylmethyl)-1-p-fluorophenyl-4-oxo-1,3,8-triazaspiro[4,5]decane
8-(4-p-fluorophenyl-2-pyridylmethyl)-1-p-chlorophenyl-4-oxo-1,3,8-triazaspiro[4,5]decane
8-(4-p-chlorophenyl-2-pyridylmethyl)-1-phenyl-4-oxo-1,3,8-triazaspiro[4,5]decane
8-(4-p-chlorophenyl-2-pyridylmethyl)-1-p-fluorophenyl-4-oxo-1,3,8-triazaspiro[4,5]decane
8-(4-p-chlorophenyl-2-pyridylmethyl)-1-p-chlorophenyl-4-oxo-1,3,8-triazaspiro[4,5]decane

EXAMPLE 2

A mixture of 1.84 g of 2-aminomethyl-4-phenylpyridine (obtainable by reduction of 2-cyano-4-phenyl-pyridine with LiAlH$_4$) and 2.15 g of 1,5-dichloro-3-phenyl-2-pentene in 40 ml of acetone and 40 ml of water is boiled for 24 hours and worked up in the customary manner. "P" dihydrochloride, m.p. 223° (decomposition) is obtained.

EXAMPLE 3

A suspension of 4-phenyl-1-(4-phenylpicolinoyl)-1,2,3,6-tetrahydropyridine (obtainable by reaction of 4-phenyl-picolinic acid with 4-phenyl-1,2,3,6-tetrahydropyridine in the presence of carbonyldiimidazole in tetrahydrofuran) in 200 ml of tetrahydrofuran is added dropwise to a suspension of 3.8 g of LiAlH$_4$ in 200 ml of tetrahydrofuran, with stirring. The mixture is stirred at 20° for a further 2 hours and worked up in the customary manner to give "P" dihydrochloride, m.p. 223° (decomposition).

The other compounds mentioned in Example 1 are obtained analogously from the corresponding acid amides.

EXAMPLE 4

3.44 g of 3-(hydroxy-4-phenyl-1-piperidylmethyl)-4-phenyl-pyridine are heated at 50° with 40 ml of 1 N hydrochloric acid for 2 hours and the mixture is worked up in the customary manner to give "P" dihydrochloride, m.p. 223° (decomposition).

EXAMPLE 5

A mixture of 10 g of 2-(4-phenyl-1,2,3,6-tetrahydropyridyl-methyl)-4-m-methoxyphenyl-pyridine and 10 g of pyridine hydrochloride is stirred at 160° for 3 hours. Customary working up gives 2-(4-phenyl-1,2,3,6-tetrahydropyridyl-methyl)-4-m-hydroxyphenyl-pyridine.

EXAMPLE 6

A suspension of 3.56 g of 2-(4-phenyl-1,2,3,6-tetrahydropyridyl-methyl)-6-m-methoxyphenyl-pyridine in 50 ml of 1,2-dichloroethane is added dropwise to a boiling solution of 15.6 g of a dimethyl sulfide-boron tribromide complex in 50 ml of 1,2-dichloroethane and the mixture is boiled for a further 30 minutes and worked up in the customary manner to give 2-(4-phenyl-1,2,3,6-tetrahydropyridyl-methyl)-6-m-hydroxyphenyl-pyridine.

The following examples relate to pharmaceutical formulations which contain amines of the formula I or their acid addition salts:

EXAMPLE A: Tablets

A mixture of 1 kg of "P" dihydrochloride, 4 kg of lactose, 1.2 kg of potato starch, 0.2 kg of talc and 0.1 kg of magnesium stearate is pressed to tablets in the customary manner such that each tablet contains 10 mg of active compound.

EXAMPLE B: Coated tablets

Tablets are pressed analogously to Example A and are then coated in the customary manner with a coating of sucrose, potato starch, talc, tragacanth and a dyestuff.

EXAMPLE C: Capsules

Hard gelatine capsules are filled with 2 kg of "P" dihydrochloride in the customary manner so that each capsule contains 20 mg of the active compound.

EXAMPLE D: Ampoules

A solution of 1 kg of "P" dihydrochloride in 60 l of doubly-distilled water is subjected to sterile filtration, filled into ampoules and lyophilized under sterile conditions and the ampoules are sealed under sterile conditions. Each ampoule contains 10 mg of active compound.

Tablets, coated tablets, capsules and ampoules which contain one or more of the other active compounds of the formula I and/or their physiologically acceptable acid addition salts are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pyridine derivative of the formula $$R^1-\overset{Z}{\underset{Z-Y}{\parallel}}\overset{C_nH_{2n}-R}{\underset{Z}{\parallel}}$$

wherein
group Y or one of the groups Z is N and the others of these groups are in each case CH;
n is 1, 2, or 3;
R is $$-N\overbrace{\phantom{XXXX}}R^2; \text{ and}$$

$R^1$ and $R^2$ are independently phenyl or 2- or 3-thienyl, or phenyl or 2- or 3-thienyl, mono- or di-substituted by alkyl or alkoxy each of 1–4 C atoms, F, Cl, Br, OH, $CF_3$ or a combination thereof;
or a physiologically acceptable salt thereof.

2. 3-Phenyl-5-(4-phenyl-piperidinomethyl)-pyridine, a compound of claim 1.

3. A compound of claim 1, wherein
$R^1$ is phenyl, tolyl, methoxyphenyl, fluorophenyl, chlorophenyl, hydroxyphenyl, trifluoromethylphenyl, dimethoxyphenyl or thienyl.

4. A compound of claim 1, wherein $R^1$ is phenyl.

5. A compound of claim 1, wherein
$R^2$ is phenyl, tolyl, methoxyphenyl, fluorophenyl, chlorophenyl, trifluoromethylphenyl, chlorotrifluoromethylphenyl or thienyl.

6. A compound of claim 1, wherein $R^2$ is phenyl.

7. A compound of claim 1, wherein
$C_nH_{2n}$ is $-CH_2-$, $-CH(CH_3)-$, $-(CH_2)_2-$ or $-(CH_2)_3-$.

8. A compound of claim 1, wherein
$R^1$ is phenyl, o-, m- or p-tolyl, m- or p-methoxyphenyl, p-fluorophenyl, p-chlorophenyl, m- or p-hydroxyphenyl, m-trifluoromethylphenyl, 3,4-dimethoxyphenyl or 2-thienyl;
$R^2$ is phenyl, o-, m- or p-tolyl, p-methoxyphenyl, p-fluorophenyl, p-chlorophenyl, m-trifluoromethylphenyl or 2- or 3-thienyl; and
$C_nH_{2n}$ is $-CH_2-$, $-CH(CH_3)-$, $-(CH_2)_2-$ or $-(CH_2)_3-$.

9. A compound of claim 1, wherein
$R^1$ and $R^2$ are identical or different and are each phenyl, p-fluorophenyl or p-chlorophenyl; and
$C_nH_{2n}$ is $-CH_2-$.

10. A compound of claim 1 which is a 2-$R^1$-6-$RC_nH_{2n}$-pyridine.

11. A compound of claim 1 which is a 2-$R^1$-4-$RC_nH_{2n}$-pyridine.

12. A compound of claim 1 which is a 3-$R^1$-5-$RC_nH_{2n}$-pyridine.

13. A compound of claim 1, which is 2-$R^1$-4-$RC_nH_{2n}$-pyridine.

14. A pharmaceutical composition comprising a therapeutic amount of a compound of claim 1, and a compatible excipient.

15. A composition of claim 14, wherein the amount of said compound is about 0.2–500 mg.

16. A method of treating schizophrenia comprising administering to a subject an amount of a compound of claim 1 effective for treating schizophrenia.

17. A method of treating depression comprising administering to a subject an antidepressive amount of a compound of claim 1.

* * * * *